United States Patent
Yamaguchi et al.

(10) Patent No.: US 8,758,743 B2
(45) Date of Patent: Jun. 24, 2014

(54) COMPOSITIONS CONTAINING COENZYME Q10

(75) Inventors: Rumi Yamaguchi, Yokkaichi (JP); Hiroaki Yamaguchi, Yokkaichi (JP); Hironobu Nanbu, Yokkaichi (JP); Lekh Raj Juneja, Yokkaichi (JP); Nagahiro Yamazaki, Yokkaichi (JP)

(73) Assignee: Taiyo Kagaku Co., Ltd., Yokkaichi-Shi (JP)

( * ) Notice: Subject to any disclaimer, the term of this patent is extended or adjusted under 35 U.S.C. 154(b) by 1045 days.

(21) Appl. No.: 10/542,203

(22) PCT Filed: Jan. 15, 2004

(86) PCT No.: PCT/JP2004/000216
§ 371 (c)(1),
(2), (4) Date: Jul. 14, 2005

(87) PCT Pub. No.: WO2004/064543
PCT Pub. Date: Aug. 5, 2004

(65) Prior Publication Data
US 2006/0134085 A1  Jun. 22, 2006

(30) Foreign Application Priority Data

Jan. 17, 2003 (JP) ................ 2003-009013
Jun. 10, 2003 (JP) ................ 2003-165690

(51) Int. Cl.
*A61K 38/43* (2006.01)

(52) U.S. Cl.
USPC ........... 424/94.1; 514/546; 514/547; 514/690

(58) Field of Classification Search
None
See application file for complete search history.

(56) References Cited

U.S. PATENT DOCUMENTS

| | | | |
|---|---|---|---|
| 4,325,942 A | 4/1982 | Taki et al. | |
| 4,707,360 A | 11/1987 | Brasey | |
| 4,751,241 A | 6/1988 | Motoyama et al. | |
| 5,382,439 A | 1/1995 | Hill et al. | |
| 6,045,826 A | 4/2000 | Borowy-Borowski et al. | |
| 6,048,566 A | 4/2000 | Behnam et al. | |

FOREIGN PATENT DOCUMENTS

| | | | |
|---|---|---|---|
| CN | 1109712 A | | 10/1995 |
| EP | 0023349 A2 | | 2/1981 |
| EP | 659347 A1 | | 6/1995 |
| EP | 1 474 992 A1 | | 11/2004 |
| EP | 1 475 363 A1 | | 11/2004 |
| EP | 1 582 206 A1 | | 10/2005 |
| EP | 1 602 286 A1 | | 12/2005 |
| JP | 55081813 A | * | 6/1980 |
| JP | 61012632 A | * | 1/1986 |
| JP | 63-150221 A | | 6/1988 |
| JP | 2000-42395 A | | 2/2000 |
| JP | 2000-212066 A | | 8/2000 |
| JP | 2001-504343 A | | 4/2001 |
| JP | 2003-125734 A | | 5/2003 |
| JP | 2003-238396 A | | 8/2003 |
| JP | 2003-300870 A | | 10/2003 |
| WO | WO 9517953 A1 | * | 7/1995 |
| WO | WO-98/21984 A1 | | 5/1998 |
| WO | WO-02/24152 A2 | | 3/2002 |
| WO | WO-02/067864 A2 | | 9/2002 |

OTHER PUBLICATIONS

Sigma-Aldrich technical bulletin on the web at http://www.sigmaaldrich.com/catalog/ p. 1, Glyceryl Tributyrate, Accessed on Feb. 23, 2009.*

* cited by examiner

*Primary Examiner* — Satyendra Singh

(74) *Attorney, Agent, or Firm* — Birch, Stewart, Kolasch & Birch, LLP (57) ABSTRACT

A coenzyme Q10-containing composition comprising a coenzyme Q10 and a hydrophilic fatty acid ester of a polyhydric alcohol; a coenzyme Q10-containing composition comprising a coenzyme Q10, a lipophilic fatty acid ester of a polyhydric alcohol and a hydrophilic fatty acid ester of a polyhydric alcohol; and a food or beverage comprising the coenzyme Q10-containing composition as defined above.

11 Claims, 2 Drawing Sheets

COMPOSITIONS CONTAINING COENZYME Q10

This application is a 371 national stage entry of international application No. PCT/JP04/00216, filed on Jan. 15, 2004, which claims priority to Japanese application No. JP 2003-009013, filed on Jan. 17, 2003 and JP 2003-165690, filed on Jun. 10 2003.

TECHNICAL FIELD

The present invention relates to a coenzyme Q10-containing composition which is suitably used especially in the field of food.

BACKGROUND ART

Coenzyme Q10 (CoQ10) is also referred to as ubidecarenone, ubiquinone-10 or the like, and has been utilized as a medicament such as a metabolic cardiotonic drug due to its specific physiological action. In addition, in Japan, the coenzyme Q10 can now be utilized in the application for food according to the revision in the classification of foods and medicines, and its application in the field of health-foods is expected. Especially the recent studies of CoQ10 have been very fruitful, and there have been reported myocardial protection action, prevention of carcinogenesis, anti-aging action, and LDL oxidation suppression in blood derived from anti-oxidative action of CoQ10, as well as suppression of elevation in blood pressure, amelioration in oxygen utilization efficiency in myocardial ischemia, ATP synthesis activation at myocardial mitochondria, cardiac function amelioration or the like. However, CoQ10 is a yellow to orange solid at an ordinary temperature, which is hardly dissolvable in water or alcohol, and is less likely to be dissolved in an oil, so that there are some disadvantages that its general-purpose for the utilization in the food use is very low, and the application to a beverage especially poses great limitation.

As a method for producing a CoQ10 preparation, there have been proposed a method for preparing an aqueous liquid preparation of a fat-soluble substance, comprising mixing a CoQ10, an emulsifying agent, a polyhydric alcohol and water, and thereafter subjecting the mixture to a high-pressure treatment (see, for example, JP 2000-212066 A), a method of solubilization using a polyoxyethylene sorbitan monooleate (see, for example, JP 2001-504343 A), and the like. However, the aqueous liquid preparation produced by the former method can temporarily obtain CoQ10 in the form of an aqueous liquid preparation by carrying out a treatment at an ultrahigh-pressure of 1000 kg/cm$^2$, but its stability is poor and becomes white turbid or precipitates crystals of CoQ10. Also, in the latter method, the polyoxyethylene sorbitan monooleate is used, and the ethylene oxide-based surfactant is not preferable for the utilization in food use because highly toxic by-products are produced in the synthetic reaction during the production process.

In addition, as a preparation having enhanced bioabsorption ratio of the CoQ10, there has been proposed a mixture of a CoQ10 and an edible oil in which a CoQ10 is dispersed in the form of crystals, obtainable by adding a thermally dissolved CoQ10 in a heated edible oil, or adding a CoQ10 to an edible oil, thermally dissolving the mixture, and then cooling the mixture (see, for example, JP 2003-125734 A). However, this preparation cannot be directly added to an aqueous food.

DISCLOSURE OF INVENTION

An object of the present invention is to provide a CoQ10-containing composition suitably applicable for food use, which has excellent storage stability and improved bioabsorbability of CoQ10.

Concretely, the present invention relates to:
[1] a coenzyme Q10-containing composition comprising a coenzyme Q10 and a hydrophilic fatty acid ester of a polyhydric alcohol;
[2] the coenzyme Q10-containing composition according to the above [1], wherein the hydrophilic fatty acid ester of a polyhydric alcohol is an organic and fatty acid ester of monoglycerol and/or a polyglycerol condensed ricinoleate;
[3] the coenzyme Q10-containing composition according to the above [1] or [2], wherein the hydrophilic fatty acid ester of a polyhydric alcohol has an HLB of 8 or more;
[4] the coenzyme Q10-containing composition according to any one of the above [1] to [3], characterized in that the composition is a coenzyme Q10 highly absorbable composition having improved bioabsorbability of coenzyme Q10 as compared to that of coenzyme Q10 alone;
[5] a coenzyme Q10-containing composition comprising a coenzyme Q10, a lipophilic fatty acid ester of a polyhydric alcohol and a hydrophilic fatty acid ester of a polyhydric alcohol;
[6] a coenzyme Q10-containing composition produced by the steps of a first step of forming a complex between a coenzyme Q10 and a lipophilic fatty acid ester of a polyhydric alcohol; and a second step of mixing the complex obtained in the first step and a hydrophilic fatty acid ester of a polyhydric alcohol;
[7] the coenzyme Q10-containing composition according to the above [5] or [6], wherein the composition is emulsified or solubilized in an oil-in-water droplet form;
[8] the coenzyme Q10-containing composition according to the above [7], wherein emulsion particles have an average emulsion particle size of 300 nm or less;
[9] the coenzyme Q10-containing composition according to any one of the above [5] to [8], wherein the lipophilic fatty acid ester of a polyhydric alcohol has an HLB of 6 or less, and the hydrophilic fatty acid ester of a polyhydric alcohol has an HLB of 8 or more;
[10] a food or beverage comprising the coenzyme Q10-containing composition as defined in any one of the above [1] to [9];
[11] a hydrophilic fatty acid ester of a polyhydric alcohol for preparing the coenzyme Q10-containing composition as defined in any one of the above [1] to [4]; and
[12] use of a hydrophilic fatty acid ester of a polyhydric alcohol for preparation of the coenzyme Q10-containing composition as defined in any one of the above [1] to [4].

BEST MODE FOR CARRYING OUT THE INVENTION

The CoQ10-containing composition of the present invention comprises mainly two embodiments. A first embodiment is a composition comprising a CoQ10 and a hydrophilic fatty acid ester of a polyhydric alcohol (hereinafter referred to as the first composition of the present invention), and a second embodiment is a composition comprising a CoQ10, a lipophilic fatty acid ester of a polyhydric alcohol and a hydrophilic fatty acid ester of a polyhydric alcohol (hereinafter referred to as the second composition of the present invention). In the present specification, the first composition of the present invention and the second composition of the present invention may be simply collectively referred to as a composition of the present invention in some cases. Also, the CoQ10-containing composition of the present invention may be referred to as a "ubidecarenone preparation" in some cases. The composition of each embodiment will be orderly explained hereinbelow.

(1) First Composition of the Present Invention

One of the great features of the first composition of the present resides in that the composition comprises a CoQ10 and a hydrophilic fatty acid ester of a polyhydric alcohol.

The shape of the composition is not particularly limited, and the composition is preferably in the form of granule, powder or liquid, from the viewpoint of convenience in use. One that is in the form of granule or powder do not have the problem of precipitation which has inherently been caused in CoQ10, so that the composition has excellent storage stability. Even when the composition is in the form of liquid, the CoQ10 is stably emulsified or solubilized by the hydrophilic fatty acid ester of a polyhydric alcohol. Therefore, for example, when the composition is stored at room temperature or the like, the crystals of the CoQ10 are less likely to be precipitated, so that the composition has excellent storage stability in the same manner as one in the form of granule or the like. In addition, the first composition of the present invention can be stably emulsified or solubilized in water for a long period of time.

When the composition is emulsified and solubilized in water, the average emulsion particle size of the emulsion particles of the CoQ10 is not particularly limited, and the average emulsion particle size is usually from 1 to 10000 nm, and the average emulsion particle size is preferably from 1 to 5000 nm, more preferably from 1 to 1000 nm, even more preferably from 1 to 500 nm, most preferably from 1 to 100 nm, from the viewpoint of improving bioabsorbability.

The average emulsion particle size can be determined by, for example, a laser diffraction-type particle size distribution analyzer (NICOMP MODEL 370, manufactured by Particle Sizing Systems).

In the CoQ10 contained in the first composition of the present invention, it is deduced that the CoQ10 is in a monodisperse state suitable for absorption when absorbed in a living body, because the crystallization of the CoQ10 can be suppressed by the emulsifying or solubilizing action of a hydrophilic fatty acid ester of a polyhydric alcohol. Therefore, the CoQ10 in the first composition of the present invention has a high bioabsorbability. In addition, the absorption of the CoQ10 into a living body is continued because the CoQ10 is enveloped with a coating film of the hydrophilic fatty acid ester of a polyhydric alcohol.

Since the first composition of the present invention can be produced using raw materials generally widely used in the filed of foods, the first composition can be suitably utilized in the application of foods. Even if the composition is added to an aqueous system, the precipitation of the CoQ10 does not substantially take place, so that the CoQ10 can be especially conveniently utilized for an aqueous food such as a beverage for which the CoQ10 has been conventionally difficult to be used.

The CoQ10 refers to a benzoquinone derivative having isoprenoid chain composed of 10 isoprene units as a side chain, and is widely distributed in nature. In animals, plants and the like, the CoQ10 is involved in the electron transport system of oxidative phosphorylation in the mitochondria. The CoQ10 used in the present invention is not particularly limited, as long as a living body, for example, a mammal, especially human can take it. As the CoQ10 used in the present invention, there may be used, for example, a generally used industrially synthesized product, a cell extract such as an yeast extract obtained by fermentation method, an extract from an animal or plant, such as sardine, pig, Bos, Gallus, broccoli, eggplant, garlic, or cabbage, or the like, each of which can be used alone or in admixture of two or more kinds. Preferably, the yeast extract obtained by the fermentation method may be used.

Incidentally, since the CoQ10 having an isoprenoid chain composed of 1 to 12 isoprene units (CoQ1-12) exists in nature, the CoQ10 of the present invention may partly contain these analogues having different lengths of isoprenoid chains so long as the exhibition of the desired effects of the present invention is not inhibited.

The term "hydrophilic" in the hydrophilic fatty acid ester of a polyhydric alcohol used in the present inventions refers to one generally having an HLB of 8 or so or more. Mainly, from the viewpoint of applicability to the aqueous foods, the HLB is preferably 8 or more, more preferably 9.5 or more, even more preferably 11 or more. Here, the phrase "HLB of 8 or so" refers to a value of an HLB such that the HLB is not exactly 8 but an HLB is a value is satisfactory in that the desired effects of the present invention can be exhibited to the same level as a fatty acid ester of a polyhydric alcohol having an HLB of at least 8. In the present specification, the method of obtaining an HLB is not particularly limited, and for example, a known method or the like as shown below can be utilized.

Incidentally, in the composition of the present invention, there may be a case where the hydrophilic fatty acid ester of a polyhydric alcohol, and a lipophilic fatty acid ester of a polyhydric alcohol described later, having an HLB of less than 8 or so, which is not considered to be "hydrophilic" in the present specification are used. When the HLB of the used ester is obtained as an average of all the HLB's of both the esters (i.e. a value obtained by dividing a total sum of the HLB of each ester molecule used in the composition by the number of the entire ester molecules), it is preferable that the average is 8 or so or more, especially 8 or more, further 9.5 or more, and more especially 11 or more.

The HLB generally refers to a measure expressing the degree of hydrophilicity and lipophilicity (hydrophobicity) of an emulsifying agent, and the stronger the hydrophilicity, the greater the value. The method of obtaining an HLB is not particularly limited. As the hydrophilic fatty acid ester of a polyhydric alcohol of the present invention, for example, there may be used one that can be acknowledged as being hydrophilic by at least one of the methods of obtaining an HLB given below. In addition, the phrase "HLB of 8 or more" in the present invention means a case where an HLB of 8 or more is shown according to any one of the methods of the following methods. The same can be said for a preferred range of HLB of 9.5 or more, or 11 or more.

As the method of obtaining an HLB, for example, known various methods such as the Griffin equation (the following formula) can be utilized.

$$HLB = 20 \times \frac{\text{Molecular Weight of Hydrophilic Moiety}}{\text{Molecular Weight of Entire Emulsifying Agents}}$$

In the above-mentioned equation, the hydrophilic moiety refers to a portion excluding the hydrocarbon chain from the entire molecule constituting the emulsifying agent (the fatty acid ester of a polyhydric alcohol in the present specification). In addition, in the case of an emulsifying agent of an ester form, the HLB can be calculated from the following equation from a saponification value and an acid value of the constituting fatty acid.

$$HLB = 20 \times (1 - S/A),$$

wherein S: saponification value, and A: acid value of the constituting fatty acid.

In addition, in the case of one only having a polyoxyethylene chain as a hydrophilic group, the HLB can be calculated by the following equation:

$$HLB = E/5,$$

wherein E: weight percentage of the polyoxyethylene group.

Besides these arithmetic methods, the HLB can also be obtained experimentally. In other words, HLB is obtained by combining an emulsifying agent having a known HLB and an emulsifying agent having an unknown HLB, emulsifying a fat or oil having a known HLB and water, selecting a mixing ratio of the best emulsification state, and calculating the HLB according to the following equation.

$$\{(Wu \times HLBu) + (Wa \times HLBa)\} / \{Wu + Wa\} = HLBo,$$

wherein Wu: a weight percentage of an emulsifying agent having an unknown HLB
Wa: a weight percentage of an emulsifying agent having a known HLB
HLBu: an HLB of an emulsifying agent having an unknown HLB (HLB of an emulsifying agent to be obtained)
HLBa: an HLB of an emulsifying agent having a known HLB
HLBo: the required HLB for a fat or oil.

The polyhydric alcohol refers to an alcohol having two or more hydroxyl groups within the same molecule. The polyhydric alcohol is not particularly limited, and for example, the polyhydric alcohol may be composed of monomers such as glycerol, or polymers such as polyglycerol. The number of polymerization of the monomers constituting the polymer (degree of polymerization) is not particularly limited. Here, when the used hydrophilic fatty acid ester of a polyhydric alcohol comprises a mixture of numerous hydrophilic fatty acid esters of a polyhydric alcohol, the degree of polymerization of the polyhydric alcohol of the used ester is obtained an average of individual kinds of esters.

The constituting fatty acid of the fatty acid ester of a polyhydric alcohol is not particularly limited, and may be a linear or branched, unsaturated or unsaturated fatty acid. In addition, the kinds of the constituting fatty acids are not particularly limited, and one or more fatty acids may be contained in one fatty acid ester of a polyhydric alcohol.

In the present invention, a hydrophilic fatty acid ester of a polyhydric alcohol which can be used in foods can be suitably used. Specific examples thereof include glycerol fatty acid esters such as organic and fatty acid esters of monoglycerol, polyglycerol fatty acid esters and polyglycerol condensed ricinoleate, sorbitan fatty acid esters, sucrose fatty acid esters, lecithins, saponins and the like, which can be used alone or in admixture of two or more kinds. Among them, as the hydrophilic fatty acid ester of a polyhydric alcohol, organic and fatty acid esters of monoglycerol and/or polyglycerol condensed ricinoleate can be suitably used, from the viewpoint of effectively suppressing the re-crystallization of the CoQ1O.

As the above-mentioned organic and fatty acid esters of monoglycerol, for example, citric and stearic acid ester of monoglycerol, acetic and stearic acid ester of monoglycerol, succinic and stearic acid ester of monoglycerol, succinic and caprylic acid ester of monoglycerol, lactic and stearic acid ester of monoglycerol, diacetyltartaric and stearic acid ester of monoglycerol, and the like are preferably used. Among them, citric and stearic acid ester of monoglycerol and diacetyltartaric and stearic acid ester of monoglycerol are more preferably used.

As the above-mentioned polyglycerol fatty acid ester, for example, one of which polyglycerol moiety has an average degree of polymerization of from 2 to 10, and constituting fatty acid is a fatty acid having 6 to 22 carbon atoms is suitably used. As specific examples of the polyglycerol fatty acid ester, triglycerol monolaurate, triglycerol monomyristate, triglycerol monooleate, triglycerol monostearate, pentaglycerol monomyristate, pentaglycerol trimyristate, pentaglycerol monooleate, pentaglycerol trioleate, pentaglycerol monostearate, pentaglycerol tristearate, pentaglycerol monostearate, hexaglycerol monocaprylate, hexaglycerol dicaprylate, hexaglycerol monolaurate, hexaglycerol monomyristate, hexaglycerol monooleate, hexaglycerol monostearate, decaglycerol monolaurate, decaglycerol monomyristate, decaglycerol monooleate, decaglycerol monopalmitate, decaglycerol monostearate, decaglycerol distearate, and the like are more preferably used.

As the above-mentioned polyglycerol condensed ricinoleate, for example, one of which polyglycerol moiety has an average degree of polymerization of from 2 to 10, and polyricioleate moiety having an average degree of condensation (average number of condensation of ricinoleic acid) of from 2 to 4 can be suitably used. Specifically, tetraglycerol condensed ricinoleate, pentaglycerol condensed ricinoleate, hexaglycerol condensed ricinoleate, diglycerol condensed ricinoleate, and the like can be more suitably used.

As the above-mentioned sorbitan fatty acid ester, for example, sorbitan monostearate, sorbitan monooleate, and the like can be suitably used.

As the above-mentioned sucrose fatty acid ester, for example, sucrose palmitate, sucrose stearate, and the like can be suitably used.

As the above-mentioned lecithin, for example, soybean lecithin, egg yolk lecithin, enzymatically decomposed lecithin, and the like can be suitably used.

As the above-mentioned saponin, for example, sophora saponin, quillaia saponin, soybean saponin, Yucca saponin, and the like can be suitably used.

The total content of the CoQ10 and the hydrophilic fatty acid ester of a polyhydric alcohol in the first composition of the present invention is not particularly limited, and the total content is preferably from 1 to 60% by weight, more preferably from 3 to 40% by weight. In addition, the ratio between the CoQ10 and the hydrophilic fatty acid ester of a polyhydric alcohol is such that the hydrophilic fatty acid ester of a polyhydric alcohol is added in an amount of preferably from 10 to 5000 parts by weight, more preferably from 40 to 3500 parts by weight, even more preferably from 40 to 500 parts by weight, based on 100 parts by weight of the CoQ10.

In the preparation of the first composition of the present invention, the hydrophilic fatty acid ester of a polyhydric alcohol as described above is used Therefore, one embodiment of the present invention encompasses a hydrophilic fatty acid ester of a polyhydric alcohol for preparing the first composition of the present invention, and use of a hydrophilic fatty acid ester of a polyhydric alcohol for the preparation of the first composition of the present invention.

In addition, the first composition of the present invention may contain other components. The other components include, for example, water, and a lipophilic fatty acid ester of a polyhydric alcohol, a fat or oil, a fat-soluble substance, and an emulsifying agent other than a fatty acid ester of a polyhydric alcohol.

Water is not particularly limited, and includes, for example, tap water, distilled water, ion-exchanged water and the like. Water can be suitably usedas a medium in a case where the composition of the present invention is obtained in the form of liquid. Incidentally, the medium is not limited to water alone. The medium is not particularly limited, as long as the medium is capable of being easily added to an aqueous food, including, for example, ethanol, glycerol, propylene glycol, liquid sugar and the like, and these media can be used alone or as a mixture of two or more kinds.

The lipophilic fatty acid ester of a polyhydric alcohol is exemplified by an ester that is used in the second composition of the present invention. When the lipophilic fatty acid ester of a polyhydric alcohol is used, it can be handled as a liquid by, for example, dissolving a CoQ10 in the lipophilic fatty acid ester of a polyhydric alcohol in advance. In addition, when the first composition of the present invention is stored for a long period of time, an effective suppression of the crystallization of the CoQ10 can be expected.

The fat or oil, and the fat-soluble substance mentioned above includes fats and oils derived from animals or plants described below, and fat-soluble substances such as vitamins. In addition, the emulsifying agent other than the fatty acid ester of a polyhydric alcohol includes known arbitrary emulsifying agents other than the fatty acid ester of a polyhydric alcohol.

When the first composition of the present invention is in the form of a liquid using, for example, water as a medium, the first composition may contain as other components a stabilizer, a preservative, a pH adjusting agent or the like generally used for foods. By containing the stabilizer or the like, the emulsion stability of the CoQ10 can be improved, whereby consequently further improving the storage stability of the first composition of the present invention. On the other hand, when the first composition of the present invention is in the form of granule or powder, the first composition may contain a water-soluble excipient such as dextrin, cyclodextrin, sodium alginate, lactose, galactooligosaccharide, galactomannase degradation product, casein, or xanthan gum. The excipient can contribute to the stabilization of the first composition of the present invention in a dry state and at the same time to effectively act in the solubilization or the like of the composition in water.

The content of the other components in the first composition of the present invention is not particularly limited, and the content may be properly adjusted within the range so as not to inhibit the exhibition of the desired effects of the present invention.

When the first composition of the present invention is in the liquid form, the first composition can be prepared by dissolving a hydrophilic fatty acid ester of a polyhydric alcohol in a medium (for example, water), and adding a CoQ10 to the solution with stirring to emulsify. The hydrophilic fatty acid ester of a polyhydric alcohol is dissolved in a medium by adding the ester to a medium heated to a temperature of equal to or higher than the melting point of the ester, or adding the ester to a medium, and thereafter heating the mixture to dissolve. The stirring and the emulsification can be carried out with, for example, a paddle stirring, Physcotron, a homomixer, a homogenizer, a high-pressure homogenizer, a beads-mill or the like. Here, the order of addition of the CoQ10 and the hydrophilic fatty acid ester of a polyhydric alcohol and the like are not particularly limited. Also, other components such as the above-mentioned stabilizer may be added at a proper point in the preparation process of the composition. In addition, in the step of emulsifying a CoQ10, the CoQ10 can be suspended or dissolved in a synthetic fat or oil such as medium-chained (number of carbon atoms: 6-8) fatty acid triglyceride; a general vegetable fat or oil obtained from soybean, rice, rapeseed, cacao, coconut palm, sesame, safflower, palm, cotton plant, peanut, avocado, ceiba, poppy, burdock, wheat, evening primrose, camellia, Indian corn, sunflower or the like; or an animal fat or oil obtained from Bos, milk, pig, sardine, mackerel, shark, Pacific saury, or codfish. Further, in the step of emulsifying a CoQ10, the CoQ10 can be emulsified together with a fat-soluble substance such as a carotenoid such as β-carotene, lycopene, astaxanthin, or zeaxanthin; or a vitamin such as vitamin A, vitamin E, vitamin K or vitamin D, and the emulsion stability and the oxidation stability of the CoQ10 can be further enhanced by using these substances together therewith.

When the first composition of the present invention is in the form of a powder, the first composition can be prepared by dissolving the above-mentioned water-soluble excipient (for example, dextrin) in a medium (for example, water) as other component in advance, adding the liquid composition obtained in the manner described above to the solution with stirring, and further properly drying the mixture. The formulation amount of the excipient is not particularly limited, and the formulation amount is preferably from 5 to 90 parts by weight or so, more preferably from 10 to 50 parts by weight or so, based on 100 parts by weight of the first composition of the present invention. The order of addition of the excipient and the liquid composition is not particularly limited. The drying method is not particularly limited, and includes, for example, spray-drying, lyophilization, plate drying and the like. The spray-drying is preferable from the viewpoint of facilitation or the like of drying.

In addition, when the first composition of the present invention is produced into the form of granule, the first composition can be prepared by molding a composition obtained in the form of powder into granule using a granulator, for example, FLOW COATER or the like.

The first composition of the present invention can be obtained by the procedures described above (the method for preparing the first composition of the present invention is not limited to the above method), and any of them have excellent storage stability. Among them, the composition in the form of granule, powder or the like has a very high storage stability. Moreover, even in a case where the resulting composition is added again to, for example water, the obtained aqueous composition has excellent emulsion or solubilization state of the same level as the composition obtained in the form of a liquid.

In the first composition of the present invention, not only those obtained in the form of liquid but also in the form obtained as granule or powder, when the composition is administered to a living body and the CoQ10 is absorbed in a living body, the CoQ10 is emulsified or solubilized, so that it is deduced that its crystallization is sufficiently suppressed. Therefore, the bioabsorbability of the CoQ10 in the first composition of the present invention is higher than a case of the CoQ10 alone. Therefore, according to the present invention, there is provided a composition characterized in that the composition is a CoQ10 high-absorbable composition having improved bioabsorbability of the CoQ10 as compared to a case of the CoQ10 alone.

(2) Second Composition of the Present Invention

The second composition of the present invention comprises a CoQ10, a lipophilic fatty acid ester of a polyhydric alcohol and a hydrophilic fatty acid ester of a polyhydric alcohol.

The CoQ10, the hydrophilic fatty acid ester of a polyhydric alcohol, and the other components that can be used in the composition, and preferred embodiments thereof and the like are the same as the above-mentioned first composition of the present invention. In addition, the preferred embodiments of the composition are the same as the above-mentioned first composition of the present invention.

The second composition of the present invention is a CoQ10-containing composition having excellent storage stability, in which the CoQ10 is stably emulsified or solubilized, and can be stably emulsified or solubilized in water for a long period of time. The composition can be added to various foods, and its form can be maintained stably for a long period of time, without increasing the degree of white turbid or causing the precipitation especially in a beverage.

In the second composition of the present invention, a lipophilic fatty acid ester of a polyhydric alcohol is used as one of essential components, which is different from the first composition of the present invention.

As the lipophilic fatty acid ester of a polyhydric alcohol used in the second composition of the present invention, one having a property of capable of stably being dispersed, emulsified or dissolved in an oil phase, which can be used for foods, can be preferably used. Here, the term "lipophilic" generally refers to one having an HLB of less than 8 or so. This definition is intended to be distinguished from the above-mentioned "hydrophilic," and the phrase "less than 8 or so" is not to be in an exact measure.

The HLB of the lipophilic fatty acid ester of a polyhydric alcohol is not particularly limited, and the HLB is preferably less than 8, more preferably 6 or less, even more preferably 4 or less.

The lipophilic fatty acid ester of a polyhydric alcohol is not particularly limited, and one capable of acting as a nonionic surfactant is suitably used.

Specific lipophilic fatty acid esters of a polyhydric alcohol usable in the present invention include one or a mixture of two or more selected from glycerol fatty acid esters such as monoglycerol mono-fatty acid esters such as monoglycerol monostearate, monoglycerol monooleate, monoglycerol monomyristate, monoglycerol monocaprylate, monoglycerol monolaurate, monoglycerol monobehenate and monoglycerol monoerucate; monoglycerol di-fatty acid esters such as monoglycerol distearate, monoglycerol dioleate, monoglycerol dicaprylate and monoglycerol dilaurate; organic and fatty acid esters of monoglycerol such as citric and stearic acid ester of monoglycerol, acetic and stearic acid ester of monoglycerol, coconut hydrogenated oil and acetic acid ester of monoglycerol, succinic and stearic acid ester of monoglycerol, succinic and caprylic acid ester of monoglycerol, lactic and stearic acid ester of monoglycerol, and diacetyltartaric and stearic acid ester of monoglycerol; monoglycerol fatty acid esters obtained from various fats and oils, such as beef tallow hydrogenated oil and fatty acid ester of monoglycerol, rapeseed hydrogenated oil and fatty acid ester of monoglycerol, soybean hydrogenated oil and fatty acid ester of monoglycerol, cottonseed oil and fatty acid ester of monoglycerol, safflower oil and fatty acid ester of monoglycerol; polyglycerol fatty acid esters such as an ester formed between a polyglycerol having an average degree of polymerization of from 2 to 10, and a fatty acid having 6 to 22 carbon atoms, and polyglycerol condensed ricinoleates, such as an ester formed between a polyglycerol having an average degree of polymerization of from 2 to 10, and a polyricinoleic acid having a degree of condensation of 2 to 4; propylene glycol fatty acid esters such as propylene glycol monostearate, propylene glycol monooleate and propylene glycol monolaurate; sorbitan fatty acid esters such as sorbitan distearate, sorbitan tristearate, sorbitan sesquioleate, sorbitan dioleate and sorbitan trioleate; lecithins such as soybean lecithin, egg yolk lecithin, enzymatically decomposable lecithin. Among them, a mixture of one of more compounds selected from the glycerol fatty acid esters is preferable, a mixture of one or more compounds selected from the monoglycerol mono-fatty acid esters, the monoglycerol di-fatty acid esters, the organic and fatty acid esters of monoglycerol (especially, acetic and fatty acid ester of monoglycerol, coconut hydrogenated oil and acetic acid ester of monoglycerol), the polyglycerol fatty acid esters (especially an ester formed between a polyglycerol having an average degree of polymerization of 2 to 10 and a fatty acid having 6 to 22 carbon atoms) and the polyglycerol condensed ricinoleates (especially an ester formed between a polyglycerol having an average degree of polymerization of 2 to 10 and a polyricinoleic acid having a degree of condensation of 2 to 4) are more preferable, the organic and fatty acid esters of monoglycerol (especially the acetic and fatty acid ester of monoglycerol, coconut hydrogenated oil and acetic acid ester of monoglycerol) are even more preferable, and concrete examples include a 50% acetylated product of the monoglycerol monostearate, and a completely acetylated product of coconut hydrogenated oil monoglyceride. The above-mentioned lipophilic fatty acid ester of a polyhydric alcohol can be used alone or in admixture of two or more kinds. When the polyglycerol fatty acid ester is used as the lipophilic fatty acid ester of a polyhydric alcohol, it is preferable that a complex of the lipophilic fatty acid ester of a polyhydric alcohol and the CoQ10 described later forms stable oil-in-water droplet emulsion particles, or one having an esterification degree of 75% or more or an HLB of 4 or less from the viewpoint of forming a solubilized state, without being particularly limited thereto.

Since the lipophilic fatty acid ester of a polyhydric alcohol as described above is used in the second composition of the present invention, one embodiment of the present invention encompasses a lipophilic fatty acid ester of a polyhydric alcohol for preparing the second composition of the present invention, and use of a lipophilic fatty acid ester of a polyhydric alcohol for the preparation of the second composition of the present invention.

The total content of the CoQ10, the lipophilic fatty acid ester of a polyhydric alcohol and the hydrophilic fatty acid ester of a polyhydric alcohol in the second composition of the present invention is not particularly limited, and the content is preferably from 2 to 60% by weight, more preferably from 5 to 50% by weight. In addition, the ratio between the CoQ10 and the lipophilic fatty acid ester of a polyhydric alcohol is such that the lipophilic fatty acid ester of a polyhydric alcohol is added in an amount of preferably from 25 to 2000 parts by weight, more preferably from 50 to 1000 parts by weight, even more preferably from 100 to 500 parts by weight, based on 100 parts by weight of the CoQ10. On the other hand, the ratio between the CoQ10 and the hydrophilic fatty acid ester of a polyhydric alcohol is such that the hydrophilic fatty acid ester of a polyhydric alcohol is added in an amount of preferably from 50 to 10000 parts by weight, more preferably from 100 to 5000 parts by weight, even more preferably from 200 to 2000 parts by weight, based on 100 parts by weight of the CoQ10.

The second composition of the present invention is prepared by mixing the CoQ10, the lipophilic fatty acid ester of a polyhydric alcohol and the hydrophilic fatty acid ester of a polyhydric alcohol, and it is preferable that a complex of the lipophilic fatty acid ester of a polyhydric alcohol and the CoQ10 described later is stable oil-in-water droplet emulsion particles, and that a lipophilic fatty acid ester of a polyhydric alcohol used at the time has an HLB of 6 or less, and a hydrophilic fatty acid ester of a polyhydric alcohol has an HLB of 8 or more, from the viewpoint of forming a solubilized state, without being particularly limited thereto.

The second composition of the present invention can be specifically prepared by mixing a CoQ10 and a lipophilic fatty acid ester of a polyhydric alcohol with stirring, and further mixing the mixture and a hydrophilic fatty acid ester of a polyhydric alcohol with stirring. The heating conditions upon stirring are preferably from 40 to 90° C., more preferably from 50° to 80° C., even more preferably from 60° to 75° C. In addition, the stirring method is not particularly limited, and paddle stirring, a homomixer, a homogenizer, or the like can be properly utilized, and the homomixer may be preferably utilized from the viewpoint of stirring efficiency and operability.

The method for preparing the second composition of the present invention is not particularly limited, and it is preferable that the composition is prepared through, for example, the following two steps:

a first step of mixing a CoQ10 and a lipophilic fatty acid ester of a polyhydric alcohol and forming a complex between the CoQ10 and the lipophilic fatty acid ester of a polyhydric alcohol; and a second step of mixing the complex obtained in the first step and a hydrophilic fatty acid ester of a polyhydric alcohol.

The formulation amount of the CoQ10 in the above-mentioned first step is not particularly limited. The content of the CoQ10 in the complex is preferably an amount of 1 to 50% by weight, more preferably from 5 to 40% by weight, even more preferably from 10 to 30% by weight. By formulating the CoQ10 in the formulation amount, the desired composition containing a sufficient amount of CoQ10 necessary for exhibiting its function can be finally obtained.

In the above-mentioned first step, a complex formed between the CoQ10 and the lipophilic fatty acid ester of a polyhydric alcohol (hereinafter referred to as complex) is obtained. Specifically, a CoQ10 is added while heating a lipophilic fatty acid ester of a polyhydric alcohol to a temperature of from 40° to 90° C. with stirring, so that a transparent complex solution can be prepared. In addition, the CoQ10 has a melting point of about 48° C., so that the reaction mixture may be heated to a temperature of preferably from 50° to 80° C., more preferably from 60° to 75° C., because of dramatically shortened time required for the preparation of the complex in consideration of the thermal stability of the CoQ10. On the other hand, when the lipophilic fatty acid ester of a polyhydric alcohol having a high melting point is used, it is desired that the mixture is maintained at a temperature equal to or higher than the melting point of the substance up to the emulsifying step described later. Here, in the complex, it is deduced that 10 isoprene side chains existing in the CoQ10 molecule and the alkyl chain of the lipophilic fatty acid ester of a polyhydric alcohol take an entangled form with each other. In addition, the stirring method is not particularly limited, and paddle stirring, a homomixer, a homogenizer, or the like can be properly utilized, and the homomixer may be preferably utilized from the viewpoint of stirring efficiency and operability.

In the above-mentioned second step, a system in which the complex can be emulsified in an oil-in-water droplet further using a hydrophilic fatty acid ester of a polyhydric alcohol is constructed. Specifically, the complex heated to a temperature of from 40° to 90° C. and the hydrophilic fatty acid ester of a polyhydric alcohol is mixed with stirring. The heating conditions of the complex is preferably from 40° to 90° C., more preferably from 50° to 80° C., even more preferably from 60° to 75° C. As to the hydrophilic fatty acid ester of a polyhydric alcohol, the temperature conditions are not particularly limited. One heated to a temperature of from 40° to 90° C. is preferable, from the viewpoint of operability in mixing and stirring. Further, the complex and the hydrophilic fatty acid ester of a polyhydric alcohol are stirred until the mixture becomes homogeneous, and the temperature during stirring is preferably from 50° to 80° C., more preferably from 60° to 75° C. In addition, the stirring method in the second step is not particularly limited, and paddle stirring, a homomixer, a homogenizer, or the like can be properly utilized, and the homomixer may be preferably utilized from the viewpoint of stirring efficiency and operability.

The hydrophilic fatty acid ester of a polyhydric alcohol used in the second step of the present invention is formulated in an amount of preferably from 1.5 to 5 parts by weight, more preferably from 2 to 3 parts by weight, based on 1 part by weight of the complex obtained in the first step of the present invention. By formulating the hydrophilic fatty acid ester of a polyhydric alcohol within the above range based on the complex, a desired capable of continuously releasing a CoQ10 can be finally obtained, in which it is deduced that the complex is enveloped with a coating film of the hydrophilic fatty acid ester of a polyhydric alcohol in the composition.

Further, in the present invention, the mixture obtained in the second step is emulsified in the form of an oil-in-water droplet (emulsifying step). When emulsified in the form of an oil-in-water droplet, it is a common knowledge that a hydrophilic surfactant is added to an aqueous base agent, and thereafter an oil-based material is mixed and emulsified with the mixture. However, in the present invention, a great feature resides in the addition of the hydrophilic fatty acid ester of a polyhydric alcohol to the complex which is an oil-based material obtained in the first step, not to the aqueous base agent. The second step of the present invention comprises carrying out the above procedures. In other words, since the complex obtained in the first step of the present invention has unsatisfactory emulsion stability in the above-mentioned conventional emulsion procedures, the complex is efficiently incorporated into a matrix constituted by an alkyl chain of the hydrophilic fatty acid ester of a polyhydric alcohol by the emulsifying procedures of the present invention, so that the complex is stably emulsified and solubilized. However, the above procedures are not intended to exclude a separate addition of the hydrophilic fatty acid ester of a polyhydric alcohol to the aqueous base agent in advance.

The aqueous base agent when emulsifying into the form of an oil-in-water droplet is not particularly limited, and includes water, an alcohol, glycerol, propylene glycol, liquid sugar and the like, which may be used alone or in admixture of two or more kinds. Especially, glycerol is preferable, and emulsion stability and liquid fluidity can be enhanced by further adding water, ethanol or the like thereto. In addition, the formulation amount of the aqueous base agent is preferably from 0.8 to 20 parts by weight, more preferably from 1 to 10 parts by weight, even more preferably from 1.2 to 2 parts by weight, based on 1 part by weight of the mixture obtained in the second step. The emulsifying method is not particularly limited, and it is preferable that each of the mixture obtained in the second step and the aqueous base agent is heated to a temperature of from 50° to 80° C. and mixed, and thereafter emulsifying the mixture. The emulsifying apparatus which can be utilized in emulsification includes homomixer, homogenizer, ultrahigh-pressure homogenizer or the like.

As described above, the second composition of the present invention obtained by emulsifying or solubilizing a CoQ10 in the form of an oil-in-water droplet is obtained. The emulsion particles in the composition have an average emulsion particle size of preferably 300 nm or less, more preferably from 1 to 100 nm, from the viewpoint of obtaining excellent physicochemical stability of the emulsion particles.

The second composition of the present invention, in addition to one prepared as described above, can further improve emulsion stability by, for example, formulating a stabilizer, a preservative, a pH adjusting agent or the like generally used for foods in the emulsifying step of the present invention. In addition, the second composition of the present invention can be produced in the form of powder or granule in the same manner as the above-mentioned first composition of the present invention. For example, when produced in the form of powder, a water-soluble excipients as mentioned above is formulated, and the mixture is dried to form powder. The drying method is not particularly limited, and includes spray-drying, lyophilization, flat plate drying or the like, and preferably spray-drying is used. When produced in the form of granule, the composition obtained in the form of powder is molded into granules by using a granulator such as FLOW COATER. The second composition of the present invention which is formed into dry powder or granule is very excellent in storage stability, and shows the original excellent emulsion state in the case where the second composition is added to an aqueous system.

The composition of the present invention can be used as a supplement of a CoQ10 to a living body by directly orally taking the composition. Also, the composition can be suitably used as a CoQ10 supplement such as CoQ10 enriched foods. Accordingly, one embodiment of the present invention provides a food or beverage comprising the composition of the present invention. Here, the food may contain a beverage in some cases.

The food or beverage of the present invention is especially subjected to a human, without intending to exclude a feed for livestock or household pet. The food or beverage subjected to human will be explained hereinbelow, and the food or beverage of the present invention encompasses the above-mentioned feed.

The food or beverage of the present invention is not particularly limited, as long as it is a food or beverage comprising the composition of the present invention. The food or beverage includes, for example, dairy products such as cow's milk, milk beverage, cheese, and adjusted powdered milk; refreshing beverages such as juices, lactic acid drink, and lactic acid bacteria drink; luxurious beverages such as coffee, black tea, and green tea; sweets such as candies, chewing gums, chocolates, cookies, biscuits, Japanese sweets, rice snacks, cakes, and pies; processed wheat products such as bread, noodles and cake mixes; desserts such as ice cream, ice candies, pudding, jelly, yogurt, and jam; seasonings such as soy sauce, sauce, soybean paste (miso), sweetening agents, spices and dressings; soups such as miso soups, clear soups, and soups; processed marine products such as fish meat ham and sausages, marine paste products, and marine canned articles; processed agricultural products such as canned agricultural articles and fruits; processed livestock products such as stock raising ham and sausage, and canned livestock articles; and various foods and beverages.

The content of the above-mentioned composition of the present invention of the food or beverage of the present invention is not particularly limited. A composition may be contained in an amount sufficient for enrichment of CoQ10, and the content may be properly determined depending upon the components of the food or beverage to which the composition of the present invention is to be applied, and the individual in which the food or beverage is taken. The content of the composition may be, for example, calculated as the CoQ10, preferably from 0.0001 to 50% by weight, more preferably from 0.001 to 20% by weight, even more preferably from 0.002 to 10% by weight.

The food or beverage of the present invention can be prepared by, for example, adding the composition of the present invention to a prepared food or beverage, or adding the composition of the present invention to the used raw materials in advance upon the preparation of those foods or beverages, or formulating the composition together therewith during the preparation process. In addition, the food of the present invention can be prepared by adding the composition of the present invention together with the materials upon cooking the food (in some cases beverage). The timing of addition and the addition method of the composition of the present invention to the food or beverage are not particularly limited, as long as the food or beverage that can exhibit the desired effects of the present invention can be obtained.

The food or beverage of the present invention contains the CoQ10 in a high level as compared to the conventional food or beverage. Since the CoQ10 is stably emulsified or solubilized, the white turbidity or the like due to precipitation of CoQ10 is not likely to take place. Especially, while much of the refreshing beverage or the like is transparent, the external appearance of the beverage comprising the composition of the present invention has transparency of the level comparable to the conventional ones. As described above, according to the composition of the present invention, the CoQ10 can be enriched in the food or beverage without worsening the external appearance of the food or beverage.

In addition, since the composition of the present invention can be expected to have excellent therapeutic, prophylactic effects and the like for various diseases and the like as described in Examples set forth below, the CoQ10 can be used as a therapeutic agent or prophylactic agent of various diseases and the like in which the CoQ10 can act as an active ingredient. Therefore, according to the present invention, there can be also provided a therapeutic agent or prophylactic agent comprising the composition of the present invention, and use of the composition of the present invention for the manufacture of the therapeutic agent or prophylactic agent. It is preferable that the therapeutic agent or prophylactic agent is in the form of preparation suitable for oral administration. The preparation can be manufactured in the form of powder, granule, tablet, pill, capsule, a liquid agent or syrup agent using a pharmacologically acceptable aid, for example, an excipient, a wetting agent, a binding agent, a stabilizer, a dilution agent or the like, according to a known method in the field of medicament. The content of the composition in the therapeutic agent or prophylactic agent is not particularly limited, and the content calculated as the CoQ10 is preferably from 0.0001 to 50% by weight, more preferably from 0.001 to 20% by weight, even more preferably from 0.002 to 10% by weight. In addition, the dose of the therapeutic agent or prophylactic agent can be properly determined based on the effective amount (amount in which the action and effects by the CoQ10 can be confirmed) for treatment or prevention of the CoQ10 as the active ingredient that can be set according to the intended diseases to be treated or prevented, and the age, the weight or the like of the patient. The dose is not particularly limited, and is preferably, for example, from 0.15 to 20 mg/kg body weight for human per day. The pharmacological effects of the therapeutic agent or prophylactic agent obtained according to the present invention can be evaluated by using, for example, a model animal such as a rat having the intended disease.

EXAMPLES

The present invention will be explained in further detail hereinbelow by means of the examples, without intending to limit the present invention thereto.

Example 1-1

The amount 2.0 g of a polyglycerol fatty acid ester (average degree of polymerization of polyglycerol: 6, HLB=14; trade name "SUNSOFT No. Q12F," hexaglycerol esters of mono-lauric acid, manufactured by Taiyo Kagaku Co., Ltd.) was added to 50.0 g of water of which temperature was 70° C., and the mixture was stirred with Physcotron (manufactured by Nichion Irika Kikai Seisakusho). Thereafter, with keeping the temperature at 70° C. and stirring the mixture with Physcotron, 5 g of a coenzyme Q10 (manufactured by Kanegafuchi Kagaku Kogyo Kabushiki Kaisha) and 43 g of a polyglycerol condensed ricinoleate (average degree of polymerization of polyglycerol: 5, degree of condensation of ricinoleic acid =2, HLB =14, manufactured by Taiyo Kagaku Co., Ltd.) were added thereto, and the mixture was stirred with Physcotron, to give a yellow, oil-in-water emulsion type coenzyme Q10-containing composition.

Example 1-2

The amount 1.2 g of an organic and fatty acid ester of glycerol (organic acid : citric acid, HLB=8.5; trade name "SUNSOFT No. 623M," citric and mono-oleic acid esters of glycerol, manufactured by Taiyo Kagaku Co., Ltd.) and 1.5 g of a polyglycerol fatty acid ester (average degree of polymerization of polyglycerol: 6, HLB=10.5; trade name "SUNSOFT No. Q18F," hexaglycerol esters of mono-stearic acid, manufactured by Taiyo Kagaku Co., Ltd.) were added to 49.3 g of water of which temperature was 60° C., and the mixture was stirred with Physcotron. Thereafter, with keeping the temperature at 70° C. and stirring the mixture with Physcotron, 5 g of a coenzyme Q10 (manufactured by Kanegafuchi Kagaku Kogyo Kabushiki Kaisha) and 43 g of a polyglycerol condensed ricinoleate (average degree of polymerization of polyglycerol: 5, degree of condensation of ricinoleic acid=2, HLB=16, manufactured by Taiyo Kagaku Co., Ltd.) were added thereto, and the mixture was stirred with Physcotron, to give a yellow, oil-in-water emulsion type coenzyme Q10-containing composition. The average emulsion particle size of the emulsion particles of the coenzyme Q10 in the composition was 20.3 nm.

Example 1-3

The amount 10.0 g of an organic and fatty acid ester of glycerol (organic acid : citric acid, HLB =9.5; trade name "SUNSOFT No. 621B," citric and mono-stearic acid esters of glycerol, manufactured by Taiyo Kagaku Co., Ltd.) and 14.0 g of a polyglycerol fatty acid ester (average degree of polymerization of polyglycerol: 10, HLB=11; trade name "SUNSOFT No. Q182S," decaglycerol esters of distearic acids, manufactured by Taiyo Kagaku Co., Ltd.) were added to 883.0 g of water of which temperature was 60° C., and the mixture was stirred with a homomixer (manufactured by TOKUSHU KIKAI KOUGYO CO., LTD.). Thereafter, with keeping the temperature at 80° C. and stirring the mixture with a homomixer, 50 g of a coenzyme Q10 (manufactured by Kanegafuchi Kagaku Kogyo Kabushiki Kaisha) and 43.0 g of a polyglycerol condensed ricinoleate (average degree of polymerization of polyglycerol: 5, degree of condensation of ricinoleic acid=2, HLB=18, manufactured by Taiyo Kagaku Co., Ltd.) were added thereto, and the mixture was stirred with a homomixer. Thereafter, 1000 g of glycerol was added thereto, and the mixture was further stirred with a homomixer. Thereafter, the mixture was led into a homogenizer (manufactured by SANWA MACHINE CO., INC), to give a yellow, oil-in-water emulsion type coenzyme Q10-containing composition. The average emulsion particle size of the emulsion particles of the coenzyme Q10 in the composition was 40.4 nm.

Example 1-4

The amount 1.5 g of a polyglycerol fatty acid ester (average degree of polymerization of polyglycerol: 6. HLB=14; trade name "SUNSOFT No. Q12F," hexaglycerol esters of mono-lauric acid, manufactured by Taiyo Kagaku Co., Ltd.) was added to 50.5 g of water of which temperature was 65° C., and the mixture was stirred with Physcotron. Thereafter, with keeping the temperature at 70° C. and stirring the mixture with Physcotron, 5 g of a coenzyme Q10 (manufactured by Kanegafuchi Kagaku Kogyo Kabushiki Kaisha) and 43 g of water were added thereto, and the mixture was stirred with Physcotron, to give a yellow, oil-in-water emulsion type coenzyme Q10-containing composition. The average emulsion particle size of the emulsion particles of the coenzyme Q10 in the composition was 241 nm.

Example 1-5

The amount 0.7 g of a polyglycerol fatty acid ester (HLB=11; trade name "SUNSOFT No. Q182S," decaglycerol esters of distearic acids, manufactured by Taiyo Kagaku Co., Ltd.) and 0.5 g of an organic and fatty acid ester of glycerol (organic acid: diacetyl tartaric acid, HLB=9; trade name "SUNSOFT No. 641D, diacetyltartaric and mono-stearic acid esters of glycerol, manufactured by Taiyo Kagaku Co., Ltd.) were added to 50.0 g of water of which temperature was 80° C., and the mixture was stirred with Physcotron. Thereafter, with keeping the temperature at 80° C. and stirring the mixture with Physcotron, 2.5 g of a coenzyme Q10 (manufactured by Kanegafuchi Kagaku Kogyo Kabushiki Kaisha) was added thereto, and the mixture was stirred with Physcotron, to give a yellow, oil-in-water emulsion type coenzyme Q10-containing composition. The average emulsion particle size of the emulsion particles of the coenzyme Q10 in the composition was 175 nm.

Example 1-6

Four-hundred grams of water was heated to 60° to 70° C. in advance, and 18.9 g of casein (trade name "ACID CASEIN EDIBLE 30/60 MESH, manufactured by MEGGLE," 1.3 g of sodium carbonate (trade name "Soda Ash Light," manufactured by Tosoh Corporation), 8.2 g of an organic acid monoglyceride (organic acid: citric acid, HLB=9.5; trade name "SUNSOFT No. 621B," citric and mono-stearic acid esters of glycerol, manufactured by Taiyo Kagaku Co., Ltd.) and 11.3 g of a polyglycerol fatty acid ester (HLB=10.5; trade name "SUNSOFT No. Q18F hexaglycerol esters of mono-stearic acid, manufactured by Taiyo Kagaku Co., Ltd.) were added thereto with stirring the mixture with Physcotron. Thereafter, the mixture was stirred with a homomixer for 30 minutes to 1 hour. Next, 40.0 g of a coenzyme Q10 (manufactured by Kanegafuchi Kagaku Kogyo Kabushiki Kaisha) and 20.3 g of dextrin (trade name "SANDEC #70," manufactured by SANWA CORNSTARCH CO., LTD) were added thereto, and the mixture was stirred with a homomixer for about 30 minutes. Thereafter, the mixture was spray-dried to form a dry powder, to give a powder product of an oil-in-water emulsion type coenzyme Q10-containing composition.

Example 1-7

The amount 16.2 g of sodium alginate (trade name "Kimitsu Algin I-3F," manufactured by KIMITSU CHEMICAL INDUSTRIES CO., LTD) was added to 400 g of water which was heated to 75° C. The amount 10.0 g of lecithin (HLB=7; trade name "SUNLECITHIN L6," purified soybean lecithin, manufactured by Taiyo Kagaku Co., Ltd.) and 9.5 g of lysolecithin (HLB=12; trade name "SUNLECITHIN A," enzymatic hydrolyzed lecithin, manufactured by Taiyo Kagaku Co., Ltd.) were added thereto, and the mixture was stirred with a homomixer. Next, with keeping the temperature at 70° C. and stirring the mixture with a homomixer, 20.0 g of a coenzyme Q10 (manufactured by Kanegafuchi Kagaku Kogyo Kabushiki Kaisha) was added thereto. The amount 44.3 g of dextrin (trade name "BLD No. 8," manufactured by SANMATSU KOGYO CO., LTD) was added thereto and dissolved with stirring the mixture with a homomixer. Thereafter, the mixture was spray-dried to form a dry powder, to give a powder product of an oil-in-water emulsion type coenzyme Q10-containing composition.

Example 1-8

The amount 88.78 g of water, 10.8 g of high fructose corn syrup, 0.18 g of citric acid and 0.04 g of trisodium citrate were mixed. Thereafter, the mixture was heated to 93° to 95° C. with stirring, and 0.2 g of the coenzyme Q10-containing composition of Example 1-3 was mixed therewith, to give a coenzyme Q10-containing beverage.

Example 1-9

One-hundred grams of flour, 60 g of margarine, 40 g of powdered sugar, 1 g of powdered salt, 1.6 g of baking powder, 30 g of whole egg, 10 g of water and 1 g of the coenzyme Q10-containing composition of Example 1-6 were mixed, and cookie dough was produced according to an ordinary method. After cutting out from a mold, the dough was baked at 160° C. for 11 to 12 minutes, to give coenzyme Q10-containing cookies.

Example 1-10

One-hundred grams of the coenzyme Q10-containing composition of Example 1-6 was granulated in FLOW COATER (manufactured by Freund Corporation) with spraying 20 g of a 1(w/v) % aqueous solution of dextrin (trade name "BLD No. 8," manufactured by SANMATSU KOGYO CO., LTD), to give a granular, coenzyme Q10-containing supplement.

Example 1-11

Ninety-nine grams of commercially available milk was mixed with 1 g of the coenzyme Q10-containing composition of Example 1-3 with refrigeration (at 4° C.), to give milk containing 25 mg of a coenzyme Q10 per 100 g.

Example 1-12

Ninety-nine grams of a commercially available tea beverage was mixed with 1 g of the coenzyme Q10-containing composition of Example 1-3 with stirring at 60° C., to give a transparent tea beverage containing 50 mg of a coenzyme Q10 per 100 g.

Example 1-13

Ninety-nine grams of commercially available mineral water was mixed with 1 g of the coenzyme Q10-containing composition of Example 1-2 which was heated to 60° C. in advance, with stirring at 60° C. After 10 minutes of stirring, the mixture was immediately cooled, to give transparent mineral water containing 50 mg of a coenzyme Q10 per 100 g.

Example 1-14

Ninety-nine grams of a commercially available coffee beverage was mixed with 1 g of the coenzyme Q10-containing composition of Example 1-3 with stirring at room temperature, to give a coffee beverage containing 25 mg of a coenzyme Q10 per 100 g.

Example 1-15

Ninety-nine grams of a commercially available black tea beverage was mixed with 1 g of the coenzyme Q10-containing composition of Example 1-2 which was heated to 65° C. in advance, with stirring at 80° C. After 10 minutes of stirring, the mixture was immediately cooled, to give a black tea beverage containing 50 mg of a coenzyme Q10 per 100 g.

Example 1-16

One serving of a commercially available consomme soup was dissolved in 150 ml of water which was heated to 95° C., and 2 g of the coenzyme Q10-containing composition of Example 1-3 was mixed therewith, to give a transparent consomme soup containing 50 mg of a coenzyme Q10 per 150 mL.

Example 1-17

Ninety-nine grams of a commercially available noodle soup was mixed with 1 g of the coenzyme Q10-containing composition of Example 1-2 which was heated to 55° C. in advance, with stirring at 80° C. After 10 minutes of stirring, the mixture was immediately cooled, to give a transparent noodle soup containing 50 mg of a coenzyme Q10 per 100 g.

Test Example 1-1

Emulsion Stability of the Coenzyme Q10-Containing Compositions and the Beverages Containing the Composition The amount 0.2 g of the coenzyme Q10-containing composition according to Example 1-2 or 1-3 was added to 100 mL of water, and thereafter the mixture was stirred, to produce a coenzyme Q10-containing water. The coenzyme Q10-containing water, the coenzyme Q10-containing beverage of Example 1-8 and, as a comparative example, a beverage produced in the same manner as in Example 1-8 by using 0.2 g of a commercially available coenzyme Q10-containing preparation were used as test samples. Immediately after the production, the emulsion state and the average emulsion particle size after 2, 4 or 6 weeks passed under refrigeration (at 4° C.) and at 40° C. under light shielding were determined. The average emulsion particle size was determined with a laser diffraction-type particle size distribution analyzer (NICOMP MODEL 370, manufactured by Particle Sizing Systems). The results are shown in Tables 1 and 2.

TABLE 1

Results of Storage under Refrigeration (at 4° C.) under Light Shielding

| Test Sample | Item | Immediately after Production | After 2 weeks | After 4 weeks | After 6 weeks |
|---|---|---|---|---|---|
| Coenzyme Q10-Containing Water (Example 1-2) | Emulsion State | Transparent | Unchanged | Unchanged | Unchanged |
| | Average Emulsion Particle Size | 20.3 nm | 20.9 nm | 21.8 nm | 22.1 nm |
| Coenzyme Q10-Containing Water (Example 1-3) | Emulsion State | Nearly Transparent | Unchanged | Unchanged | Unchanged |
| | Average Emulsion Particle Size | 40.4 nm | 42.0 nm | 43.6 nm | 43.9 nm |
| Coenzyme Q10-Containing Beverage (Example 1-8) | Emulsion State | Nearly Transparent | Unchanged | Unchanged | Unchanged |
| | Average Emulsion Particle Size | 40.1 nm | 39.8 nm | 38.2 nm | 37.4 nm |
| Coenzyme Q10-Containing Beverage (Comparative Example) | Emulsion State | White Turbidity | Neck Ring Formation | Neck Ring Formation | Neck Ring Formation |
| | Average Emulsion Particle Size | 275.6 nm | 301.0 nm | 300.2 nm | 298.5 nm |

TABLE 2

Results of Storage at 40° C. under Light Shielding

| Test Sample | Item | Immediately after Preparation | After 2 weeks | After 4 weeks | After 6 weeks |
|---|---|---|---|---|---|
| Coenzyme Q10-Containing Water (Example 1-2) | Emulsion State | Transparent | Unchanged | Unchanged | Unchanged |
| | Average Emulsion Particle Size | 20.3 nm | 20.4 nm | 20.9 nm | 21.2 nm |
| Coenzyme Q10-Containing Water (Example 1-3) | Emulsion State | Nearly Transparent | Unchanged | Unchanged | Unchanged |
| | Average Emulsion Particle Size | 40.4 nm | 38.3 nm | 42.1 nm | 40.0 nm |
| Coenzyme Q10-Containing Beverage (Example 1-8) | Emulsion State | Nearly Transparent | Unchanged | Unchanged | Unchanged |
| | Average Emulsion Particle Size | 40.1 nm | 38.0 nm | 40.3 nm | 39.8 nm |
| Coenzyme Q10-Containing Beverage (Comparative Example) | Emulsion State | White Turbidity | Neck Ring Formation | Neck Ring Formation | Neck Ring Formation |
| | Average Emulsion Particle Size | 275.6 nm | 303.5 nm | 298.6 nm | 292.3 nm |

In addition, the powder products of Examples 1-6 and 1-7 and a coenzyme Q10 itself (manufactured by Kanegafuchi Kagaku Kogyo Kabushiki Kaisha) were used as test samples, and the storage states before the beginning of storage, and after storage at 50° C. for 4 weeks or 12 weeks passed under light shielding were confirmed. The results are shown in Table 3.

TABLE 3

Results of Storage at 50° C. under Light Shielding

| Test Sample | Item | Before the Beginning of Storage | After 4 weeks | After 12 weeks |
|---|---|---|---|---|
| Powder Product of Example 1-6 | Storage State | Yellow Powder | Yellow Powder | Yellow Powder |
| Powder Product of Example 1-7 | Storage State | Yellow Powder | Yellow Powder | Yellow powder |
| Coenzyme Q10 Powder | Storage State | Yellow Powder | Melted | Melted |

It can be seen from the results of Tables 1 and 2 that the coenzyme Q10-containing waters (Examples 1-2 and 1-3) and the coenzyme Q10-containing beverage (Example 1-8), which are the inventive products, are not found to show any particular changes in emulsion state or the like even after 6 weeks passed, so that the inventive products are in a very stable, emulsified or solubilized state. In addition, it can be seen from the results of Table 3 that the powder products of the coenzyme Q10-containing compositions (Examples 1-6 and 1-7), which are the inventive products, show very high storage stability as compared to that of the coenzyme Q10 itself.

Here, the coenzyme Q10 content of the coenzyme Q10-containing water of Example 1-3 stored at 40° C. was determined. As a result, the residual ratio of a coenzyme Q10 after 6 weeks passed was as high as 85.2% by weight. In addition, the coenzyme Q10 content of the powder product of the coenzyme Q10-containing composition of Example 1-6 stored at 50° C. was determined. As a result, the residual ratio of a coenzyme Q10 after 12 weeks passed showed a high value of 96.5% by weight.

Test Example 1-2

Stability of Foods Containing Coenzyme Q10-Containing Composition

The states immediately after production and after 8 hours passed at room temperature (25° C.) for the foods containing the coenzyme Q10-containing composition of Examples 1-8 to 1-17 were visually evaluated. Here, those products produced in the same manner as in each Example by using a coenzyme Q10 itself melted so as to have the same coenzyme Q10 content in place of the coenzyme Q10-containing composition used in each of Examples, which is the inventive product, were evaluated in the same manner as control products corresponding to each of Examples 1-8 to 1-17.

As a result, while a coenzyme Q10 floated immediately after preparation in all corresponding control products and coenzyme Q10 crystals were precipitated out when 8 hours passed, no change in state was found at all immediately after production and after 8 hours passed in each of the liquid foods such as the beverages of Example 1-8 and 1-11 to 1-17. In addition, no problem was found in the solid foods of Examples 1-9 and 1-10. As described above, it was confirmed that the coenzyme Q10-containing composition-containing foods, which are the inventive products, have totally the same properties as those of the original foods, in which the foods are enriched with a coenzyme Q10 without causing any change in the properties.

Especially, the beverages obtained in Examples included transparent beverages, and the inherent transparency was not lost by adding the coenzyme Q10-containing composition. This is thought to be due to the fact that a coenzyme Q10 is emulsified or solubilized very stably in the added coenzyme Q10-containing composition. As described above, since the coenzyme Q10-containing composition, which is the inventive product, can be added to an aqueous system, and versatility of the composition could be confirmed, without accompanying any difficulty in production of the foods containing the composition.

Test Example 1-3

Bioabsorbability Test 1 of Coenzyme Q10

The bioabsorbability of a coenzyme Q10 was evaluated by administering each of the powder product of Example 1-6 and a coenzyme Q10 itself to a rat as a test sample, sampling blood over time, and measuring the coenzyme Q10 concentration in the plasma, and the bioabsorbability was compared among the test samples.

(Test Samples and Feeding Conditions)

The test samples were administered to rats in the administration forms shown in the following Table 4. The rats were allowed to take the feed ad libitum. Here, CMC—Na stands for sodium salt of carboxymethylcellulose.

TABLE 4

| Test Sample | | Administration Form |
|---|---|---|
| Sample 1 | Powder Product of Example 1-6 | Solution of distilled water |
| Comparative Sample 1 | Coenzyme Q10 powder | Solution of soybean oil |
| Comparative Sample 2 | Coenzyme Q10 powder | Suspension of 0.5(w/v)% aqueous CMC-Na solution |

The sample 1 was prepared by adding the powder product of Example 1-6 to distilled water and mixing. The comparative sample 1 was prepared by heating a coenzyme Q10 itself to dissolve, and thereafter mixing with soybean oil. The comparative sample 2 was prepared by adding a coenzyme Q10 itself to a 0.5(w/v)% aqueous CMC—Na solution and subjecting the mixture to ultrasonication.

The conditions and the like for this test are listed hereinbelow.

Rat: Crj-SD line, 6-week old, male, n=4
Dose: The test samples calculated as 30 mg of a coenzyme Q10 per 1 kg of the body weight of a rat were administered.
Amount of administered liquid: The sample 1 and the comparative sample 2 were administered in an amount of 10 mL per 1 kg of the body weight of a rat, and the comparative sample 2 was administered in an amount of 3 mL per 1 kg of the body weight of a rat.
Method of administration: The sample was forcibly orally administered with using a stomach probe.
Blood sampling: Blood was sampled in an amount of about 0.5 mL from jugular using heparin-containing syringe.
Time of blood sampling: The blood was sampled after 1, 2, 4, 8 and 24 hours after the administration.
Processing of blood: The blood was stored with ice-cooling since immediately after the blood sampling, and centrifuged at 4° C. immediately after the termination of blood sampling, to separate the plasma. The separated plasma was dispensed in a storage container, and thereafter stored at −80° C. until use.

Method of quantification: The coenzyme Q10 concentration in the plasma was quantified by high-performance liquid chromatography (HPLC) after a liquid-liquid extraction according to the method shown hereinbelow. Specifically, 0.01 mL of a 1(w/v)% aqueous $FeCl_3$ solution, 0.5 mL of ion-exchanged water and 2 mL of methanol were added to 0.2 mL of the plasma, and the mixture was mixed. Three milliliters of hexane was added to the resulting mixed solution. The mixture was mixed, and the coenzyme Q10 was extracted. Hexane was separated from the extract. After the mixture was allowed to evaporate to dryness, the dried substances were redissolved in 0.2 mL of ethanol, and quantification was carried out.

(Conditions for HPLC)
Detector: Ultraviolet absorptiometer
Detecting wavelength: 275 nm
Column: YMC-Pack ODS-A303
(manufactured by YMC Co., Ltd.)
Mobile-phase: methanol: hexane=88:12 (ratio by volume)
Flow rate: 1 mL/minute
Analyzing time period: 40 minutes The measurement results of the coenzyme Q10 concentration in the plasma of 1 to 24 hours after administration of the sample 1, the comparative sample 1 or the comparative sample 2 are shown in Table 5 and FIG. 1.

TABLE 5

|  | Test Sample | Administration form |
|---|---|---|
| Sample 1 | Powder Product of Example 1-6 | Solution of distilled water |
| Comparative Sample 1 | Coenzyme Q10 powder | Solution of soybean oil |
| Comparative Sample 2 | Coenzyme Q10 powder | Suspension of 0.5(w/v)% aqueous CMC-Na solution |

Figure 1:
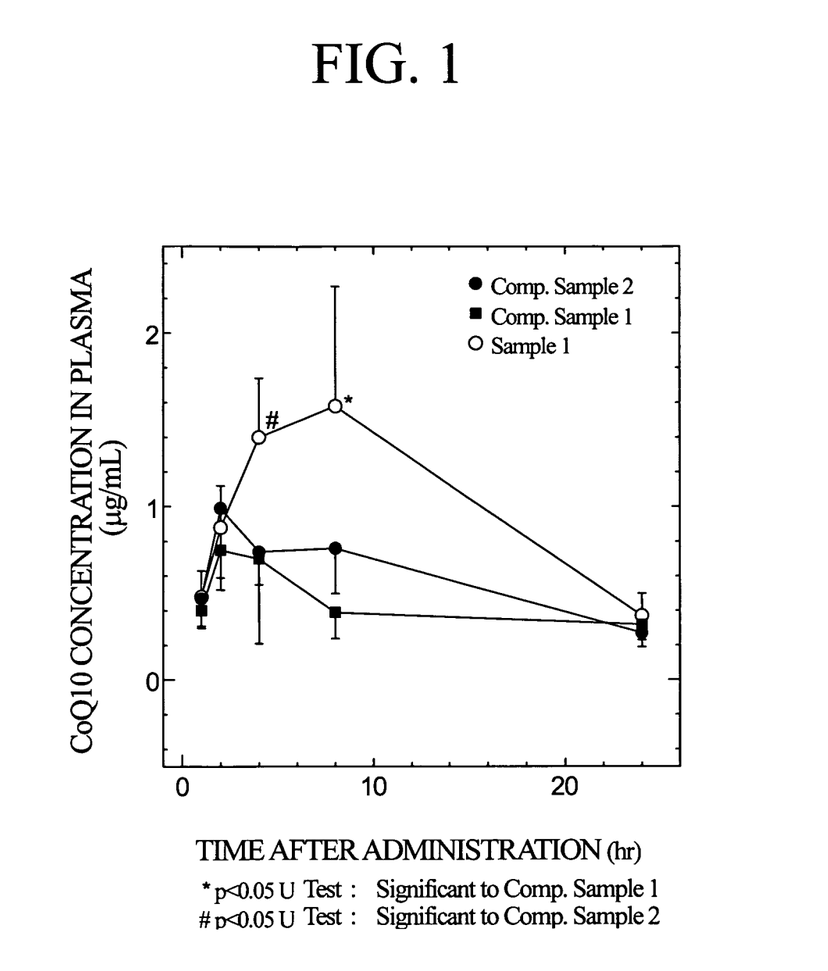
FIG. 1 is a graph showing the measurement results of the coenzyme Q10 concentration in the plasma of 1 to 24 hours after administration of each test sample to rats in Bioabsorbability Test 1.

When the sample 1 was administered, the coenzyme Q10 concentration in the plasma remained high from 4 to 8 hours after the administration, and was highest (Tmax) after 8 hours. On the other hand, when the comparative samples were administered, Tmax appeared 2 hours after the administration. The administration of the sample 1 showed a sustaining pattern of the coenzyme Q10 concentration in blood.

In addition, the highest concentration (Cmax) in the plasma in the administration of the sample 1 was 2.1 times that of the comparative sample 1 and 1.6 times that of the comparative sample 2. The integral value of the concentration in the plasma in the administration of the sample 1 from 1 to 24 hours ($AUC_{1-24}$) was 2.5 times that of the comparative sample 1, and 1.8 times that of the comparative sample 2.

It can be seen from the above results that when the test sample was administered in an amount of 30 mg per 1 kg of the body weight of a rat calculated as the amount of the coenzyme Q10, the sample 1 shows high bioabsorbability of the coenzyme Q10 as compared to those of the comparative samples 1 and 2.

Test Example 1-4

Bioabsorbability Test 2 of Coenzyme Q10

The bioabsorbability of a coenzyme Q10 was evaluated by administering each of the coenzyme Q10-containing composition of Example 1-2 and a coenzyme Q10 itself to a rat as a test sample, sampling blood over time, and measuring the coenzyme Q10 concentration in the plasma, and the bioabsorbability was compared among the test samples.

(Test Samples and Feeding Conditions)
The test samples were administered to rats in the administration forms shown in the following Table 6. The feeding conditions were set in 2 ways; a case where rats were allowed to take the feed ad libitum (satiation), and a case where rats were made to fast since the early-evening of the previous day of the test, and where the rats were fed again after blood sampling of 8 hours after the administration of the test sample.

TABLE 6

|  |  | Test Sample | Feeding Conditions | Administration Form |
|---|---|---|---|---|
| Test | A | Composition of Example 1-2 | Satiation | Solution of Distilled Water |
| Comparative Test | B | Coenzyme Q10 Powder |  | Suspension of 0.5(w/v)% Aqueous CMC-Na Solution |
| Test | A' | Composition of Example 1-2 | Fasting | Solution of Distilled Water |
| Comparative Test | B' | Coenzyme Q10 Powder |  | Suspension of 0.5(w/v)% Aqueous CMC-Na Solution |

The solution of distilled water in Tests A and A' was prepared by adding the coenzyme Q10-containing composition of Example 1-2 to distilled water and mixing the mixture. The suspension of a 0.5(w/v)% aqueous CMC—Na solution in Tests B and B' was prepared by adding a coenzyme Q10 itself to a 0.5(w/v)% aqueous CMC-Na solution and subjecting the mixture to ultrasonication.

The conditions and the like for this test are listed hereinbelow.
Rat: SD line, 7-week old, male, n=4
Dose: The test samples calculated as 5 mg of a coenzyme Q10 per 1 kg of the body weight of a rat were administered.
Amount of administered liquid: The suspension or the solution used in Tests A, A', B, or B' was administered in an amount of 5 mL per 1 kg of the body weight of a rat.
Method of administration, blood sampling, time of blood sampling, processing of blood and method of quantification were same as those in the above-mentioned Test Example 1-3.

The measurement results of the coenzyme Q10 concentration in the plasma of 1 to 24 hours after administration of each of the test samples in Tests A and B and Tests A' and B' are shown in Table 7. The measurement results in Tests A and A' and Comparative Tests B and B' are shown in the form of a graph in FIG. 2.

TABLE 7

| | | Coenzyme Q10 concentration in plasma (μg/mL) | | | | | |
|---|---|---|---|---|---|---|---|
| | | 1 hour | 2 hours | 4 hours | 8 hours | 24 hours | $AUC_{1-24}$ |
| Test | A | 0.63 ± 0.21 | 0.50 ± 0.18 | 0.27 ± 0.06 | 0.19 ± 0.05 | 0.12 ± 0.05 | 5.02 ± 1.28 |
| Comparative Test | B | 0.12 ± 0.07 | 0.17 ± 0.11 | 0.26 ± 0.09 | 0.27 ± 0.09 | 0.11 ± 0.04 | 4.78 ± 1.31 |

TABLE 7-continued

| | | Coenzyme Q10 concentration in plasma (μg/mL) | | | | | |
|---|---|---|---|---|---|---|---|
| | | 1 hour | 2 hours | 4 hours | 8 hours | 24 hours | $AUC_{1-24}$ |
| Test | A' | 0.21 ± 0.09 | 0.19 ± 0.05 | 0.11 ± 0.05 | 0.09 ± 0.05 | 0.06 ± 0.04 | 2.24 ± 0.95 |
| Comparative Test | B' | 0.03 ± 0.01 | 0.03 ± 0.01 | 0.03 ± 0.00 | 0.03 ± 0.01 | 0.04 ± 0.11 | 0.78 ± 0.30 |

Figure 2:
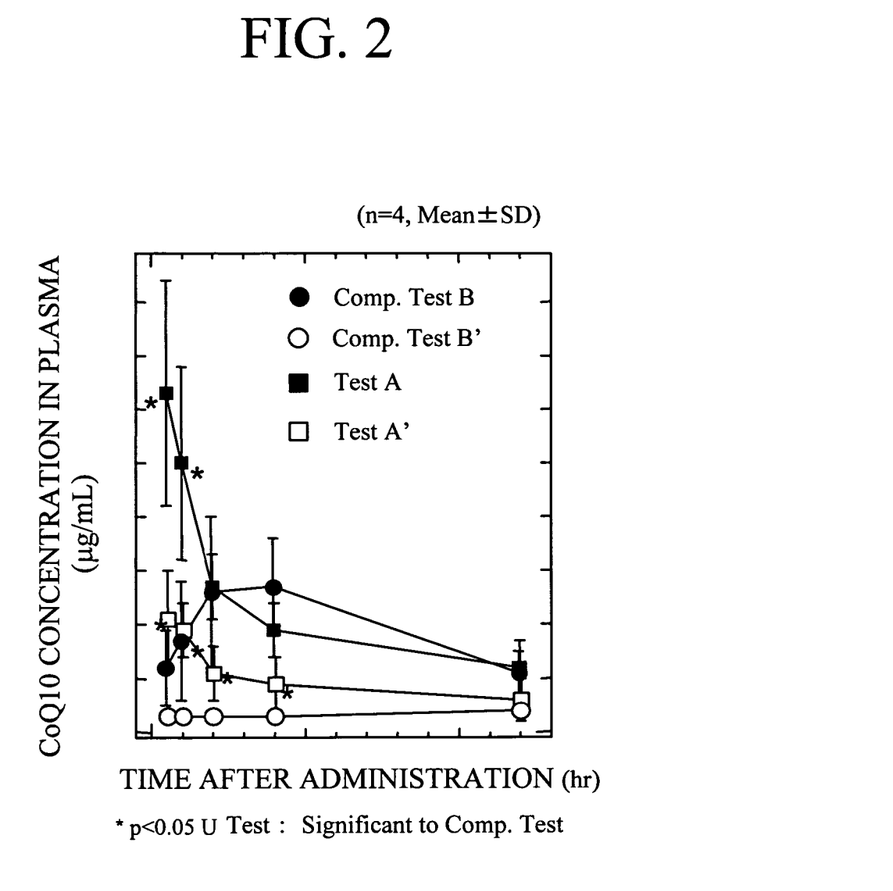
FIG. 2 is a graph showing the measurement results of the coenzyme Q10 concentration in the plasma of 1 to 24 hours after administration of each test sample in Tests A and A' and Comparative Tests B and B' to rats in Bioabsorbability Test 2.

It can be seen from the results of Table 7 and FIG. 2 that the coenzyme Q10-containing composition (Example 1-2), which is the inventive product, deduced to form emulsion-film has a very high absorption rate as compared to that of the coenzyme Q10 alone. As described above, since the absorbability is improved, an even stronger effect not only on those diseases on which the coenzyme Q10 has been reported to have an effect such as heart diseases (for example, congestive heart failure, angina pectoris, myocardial infarction and the like), hypertension, diabetes, cancer, gingival diseases, nerve diseases (for example, Parkinson disease, Alzheimer disease, Huntington disease), progressive muscular dystrophy, allergy (for example, atopic dermatitis), infertility, AIDS, chronic pulmonary disease (for example, chronic obstructive pulmonary disease, cataplectic fibroid lung and the like), but also on reviviscence or wrinkle-amelioration action, postoperative cure (for example, surgical operation, PTCA and the like) can be expected.

Example 2-1

<Ubidecarenone Preparation>
<First Step>

Fifteen grams of a monoglycerol palm hydrogenated oil acetate (trade name "SUNFAT U-12," HLB=1.5, manufactured by Taiyo Kagaku Co., Ltd.) was heated to 50° C., and 5 g of ubidecarenone (manufactured by Kanegafuchi Kagaku Kogyo Kabushiki Kaisha) which was heated to 55° C. in advance was gradually added thereto with stirring with Physcotron, to give a yellow, transparent ubidecarenone complex.

<Second Step and Emulsification Step>

With heating 20 g of the ubidecarenone complex to 50° C., 54 g of a polyglycerol condensed ricinoleate (average degree of polymerization of polyglycerol: 5, degree of condensation of ricinoleic acid=2, HLB=14, manufactured by Taiyo Kagaku Co., Ltd.) and 6 g of a polyglycerol condensed ricinoleate (average degree of polymerization of polyglycerol: 5, degree of condensation of ricinoleic acid=2, HLB=16, manufactured by Taiyo Kagaku Co., Ltd.) which were heated to 50° C. in advance were added thereto, and the mixture was stirred with Physcotron until the mixture became homogeneous. Thereafter, 100 g of glycerol, 15 g of water and 5 g of ethanol were sequentially added to the resulting mixture, with keeping the mixture at 50° C. and stirring the mixture with Physcotron, to give a yellow, transparent oil-in-water emulsion type ubidecarenone preparation. The average emulsion particle size of the emulsion particles of the ubidecarenone in the preparation was 52.0 nm.

Example 2-2

<Ubidecarenone Preparation>
<First Step>

Nineteen grams of monoglycerol monolaurate (trade name "SUNSOFT No. 750," HLB=5.3, manufactured by Taiyo Kagaku Co., Ltd.) was heated to 65° C. to melt, and 1 g of ubidecarenone (manufactured by Kanegafuchi Kagaku Kogyo Kabushiki Kaisha) was gradually added thereto with stirring with Physcotron, to give a yellow, transparent ubidecarenone complex.

<Second Step and Emulsification Step> Twenty-five grams of a monoglycerol monostearic acid diacetyl tartaric acid ester (trade name "SUNSOFT 641C," HLB=10, manufactured by Taiyo Kagaku Co., Ltd.) and 35 g of decaglycerol distearate (trade name "SUNSOFT Q-182S," HLB=11, manufactured by Taiyo Kagaku Co., Ltd.) were heated to 80° C. to melt in advance, and 20 g of the ubidecarenone complex was added thereto with stirring with Physcotron. Thereafter, 100 g of glycerol and 20 g of water were added to the resulting mixture, with keeping the resulting mixture at 65° C. and stirring the mixture with Physcotron, to give a yellow, transparent oil-in-water emulsion type ubidecarenone preparation. The average emulsion particle size of the emulsion particles of the ubidecarenone in the preparation was 80.7 nm.

Example 2-3

<Ubidecarenone Preparation>
<First Step>

Seventeen grams of pentaglycerol trioleate (trade name "SUNSOFT A-173E," HLB=7, manufactured by Taiyo Kagaku Co., Ltd.) was heated to 45° C., and 3 g of ubidecarenone (manufactured by Kanegafuchi Kagaku Kogyo Kabushiki Kaisha.) which was heated to 65° C. in advance was gradually added thereto with stirring, to give a yellow, transparent ubidecarenone complex.

<Second Step and Emulsification Step>

Sixty grams of pentaglycerol monomyristate (trade name "SUNSOFF A-141E," HLB=13, manufactured by Taiyo Kagaku Co., Ltd.) was added to 20 g of the ubidecarenone complex, and the mixture was stirred with a homomixer with keeping the temperature at 45° C. Thereafter, the resulting mixture was added to 100 g of glycerol which was separately heated to 50° C., with stirring with a homomixer, to give an emulsion. The emulsion was further homogenized with Physcotron, and thereafter 6 g of ethanol was added thereto, to give a yellow, transparent oil-in-water emulsion type ubidecarenone preparation. The average emulsion particle size of the emulsion particles of the ubidecarenone in the preparation was 125 nm.

Example 2-4

<Ubidecarenone Preparation>

Two-hundred grams of water was heated to 65° to 70° C. in advance, and 50 g of dextrin (BLDNo.8, manufactured by SANMATSU KOGYO CO., LTD) was added thereto to dissolve with stirring with Physcotron. Ten grams of the ubidecarenone preparation of Example 2-3 was gradually added thereto with keeping the temperature at 65° to 70° C., and the mixture was emulsified. Thereafter the mixture was spray-dried to give a dry powder, to give a powder product of an oil-in-water emulsion type ubidecarenone preparation.

Example 2-5

<Food Containing the Ubidecarenone Preparation>

The amount 88.78 g of water, 10.8 g of high fructose corn syrup, 0.18 g of citric acid and 0.04 g of trisodium citrate were mixed, and thereafter the mixture was heated to 93° to 95° C. with stirring. The amount 0.2 g of the ubidecarenone preparation of Example 2-1 which was heated to 60° C. in advance was added thereto, and the mixture was mixed, to give a transparent, ubidecarenone-containing beverage.

Example 2-6

<Food Containing the Ubidecarenone Preparation>

One-hundred grams of flour, 60 g of margarine, 40 g of powdered sugar, 1 g of powdered salt, 1.6 g of baking powder and 30 g of whole egg, 10 g of water and 1 g of the ubidecarenone preparation of Example 2-4 were mixed, to produce cookie dough. After cutting out from a mold, the dough was baked at 180° C. for 11 to 12 minutes, to give ubidecarenone-containing cookies.

Example 2-7

<Food Containing the Ubidecarenone Preparation>

One-hundred grams of the ubidecarenone preparation of Example 2-4 was granulated in FLOW COATER (manufactured by Freund Corporation) with spraying 20 g of 1% dextrin (BLD No. 8, manufactured by SANMATSU KOGYO CO., LTD), to give a granular ubidecarenone-containing supplement.

Example 2-8

<Food Containing the Ubidecarenone Preparation>

Ninety-nine grams of commercially available milk was mixed with 1 g of the ubidecarenone preparation of Example 2-1 which was heated to 60° C. in advance, with stirring at 60° C., to give milk containing 25 mg of ubidecarenone/100 g.

Example 2-9

<Food Containing the Ubidecarenone Preparation>

Ninety-nine grams of a commercially available tea beverage was mixed with 1 g of the ubidecarenone preparation of Example 2-1 which was heated to 60° C. in advance, with stirring at 60° C. After 10 minutes of stirring, the mixture was immediately cooled, to give a transparent tea beverage containing 25 mg of ubidecarenone/100 g.

Example 2-10

<Food Containing the Ubidecarenone Preparation>

Ninety-nine grams of a commercially available mineral water was mixed with 1 g of the ubidecarenone preparation of Example 2-1 which was heated to 60° C. in advance with stirring at 60° C. After 10 minutes of stirring, the mixture was immediately cooled, to give a transparent mineral water containing 25 mg of ubidecarenone/100 g.

Example 2-11

<Food Containing the Ubidecarenone Preparation>

Ninety-nine grams of a commercially available coffee beverage was mixed with 1 g of the ubidecarenone preparation of Example 2-2 which was heated to 65° C. in advance with stirring at 70° C. After 10 minutes of stirring, the mixture was immediately cooled, to give a coffee beverage containing 5 mg of ubidecarenone/100 g.

Example 2-12

<Food Containing the Ubidecarenone Preparation>

Ninety-nine grams of a commercially available black tea beverage was mixed with 1 g of the ubidecarenone preparation of Example 2-2 which was heated to 65° C. in advance, with stirring at 80° C. After 10 minutes of stirring, the mixture was immediately cooled, to give a black tea beverage containing 5 mg of ubidecarenone/100 g.

Example 2-13

<Food Containing the Ubidecarenone Preparation>

One serving of a commercially available consomme soup was dissolved in 150 ml of water which was heated to 95° C., and 1 g of the ubidecarenone preparation of Example 2-2 was mixed therewith, to give a transparent consomme soup containing 5 mg of ubidecarenone/150 ml.

Example 2-14

<Food Containing the Ubidecarenone Preparation>

Ninety-nine grams of a commercially available noodle soup was mixed with 1 g of the ubidecarenone preparation of Example 2-3 which was heated to 55° C. in advance with stirring at 80° C. After 10 minutes of stirring, the mixture was immediately cooled, to give a transparent noodle soup containing 15 mg of ubidecarenone/100 g.

Test Example 2-1

<Storage Stability of the Ubidecarenone Preparation and the Beverages Containing the Preparation>

The amount 0.2 g of each of the ubidecarenone preparations of Examples 2-1 to 2-3 which was heated to 50° C. was added to 100 ml of water of which temperature was 50° C., and thereafter the mixture was stirred, to prepare a ubidecarenone-containing water. The emulsion state and the average emulsion particle size immediately after the production, after 1 day, 2 weeks or 4 weeks passed at room temperature and at 50° C. were confirmed for the ubidecarenone-containing water, the ubidecarenone-containing beverage of Example 2-5, and a beverage prepared as a comparative example by using 0.1 g of a 5% by weight ubidecarenone preparation of other companies in the same manner as in Example 2-5. The average emulsion particle size was determined with the above-mentioned laser diffraction-type particle size distribution analyzer (NICOMP MODEL370). The results are shown in Tables 8 and 9.

TABLE 8

Storage Stability of Ubidecarenone Preparation (Storage at Room Temperature)

| Test Sample | Item | Immediately After Production | After 1 Day | After 2 weeks | After 4 weeks |
|---|---|---|---|---|---|
| Ubidecarenone-Containing Water (Example 2-1) | Emulsion State | Transparent | Unchanged | Unchanged | Unchanged |
| | Average Emulsion Particle Size | 52.0 nm | 50.5 nm | 61.3 nm | 66.8 nm |
| Ubidecarenone-Containing Water (Example 2-2) | Emulsion State | Slightly White Turbidity Emulsified | Unchanged | Unchanged | Unchanged |
| | Average Emulsion Particle Size | 80.7 nm | 95.1 nm | 82.8 nm | 87.4 nm |
| Ubidecarenone-Containing Beverage (Example 2-3) | Emulsion State | Slightly White Turbidity Emulsified | Unchanged | Unchanged | Unchanged |
| | Average Emulsion Particle Size | 125 nm | 137 nm | 128 nm | 132 nm |
| Ubidecarenone-Containing Beverage (Example 2-5) | Emulsion State | Transparent | Unchanged | Unchanged | Unchanged |
| | Average Emulsion Particle Size | 21.9 nm | 33.2 nm | 45.0 nm | 38.3 nm |
| Beverage of Comparative Example | Emulsion State | White Turbidity | Neck Ring Formation | Neck Ring Formation | Neck Ring Formation |
| | Average Emulsion Particle Size | 275.6 nm | 430.0 nm | 301.0 nm | 300.2 nm |

TABLE 9

Emulsion Stability of the ubidecarenone preparation (Storage at 50° C.)

| Test Sample | Item | Immediately After Production | After 1 day | After 2 weeks | After 4 weeks |
|---|---|---|---|---|---|
| Ubidecarenone-Containing Water (Example 2-1) | Emulsion State | Transparent | Unchanged | Unchanged | Unchanged |
| | Average Emulsion Particle Size | 45.8 nm | 63.0 nm | 52.9 nm | 51.6 nm |
| Ubidecarenone-Containing Water (Example 2-2) | Emulsion State | Slightly White Turbidity Emulsified | Unchanged | Unchanged | Unchanged |
| | Average Emulsion Particle Size | 77.8 nm | 81.2 nm | 88.0 nm | 85.5 nm |
| Ubidecarenone-Containing Water (Example 2-3) | Emulsion State | Slightly White Turbidity Emulsified | Unchanged | Unchanged | Unchanged |
| | Average Emulsion Particle Size | 98.6 nm | 95.4 nm | 91.3 nm | 89.7 nm |
| Ubidecarenone-Containing Beverage (Example 2-5) | Emulsion State | Transparent | Unchanged | Unchanged | Unchanged |
| | Average Emulsion Particle Size | 16.5 nm | 18.4 nm | 17.3 nm | 17.1 nm |
| Beverage of Comparative Example | Emulsion State | White Turbidity | Neck Ring Formation | Neck Ring Formation | Neck Ring Formation |
| | Average | 275.6 nm | 303.5 nm | 300.6 nm | 298.6 nm |

TABLE 9-continued

Emulsion Stability of the ubidecarenone preparation (Storage at 50° C.)

| Test Sample | Item | Immediately After Production | After 1 day | After 2 weeks | After 4 weeks |
|---|---|---|---|---|---|
| | Emulsion Particle Size | | | | |

It was confirmed from Tables 8 and 9 that the ubidecarenone-containing waters of Examples 2-1 to 2-3 exhibit very stable emulsion or solubilized states. Here, the ubidecarenone content of the ubidecarenone-containing beverage of Example 2-5 stored at 50° C. was determined. As a result, the residual ratio of the ubidecarenone after 4 weeks passed was as high as 91.4% by weight.

Test Example 2-2

<Storage Stability of the Ubidecarenone Preparation-Containing Food (Beverage)>

The properties and states were visually evaluated for the ubidecarenone preparation-containing foods according to Examples 2-8 to 2-14 immediately after the production and after 8 hours passed at room temperature. Here, one prepared by dissolving ubidecarenone alone was used in place of the ubidecarenone preparation used in each Example, so as to have the same ubidecarenone content was evaluated in the same manner as a control product corresponding to each of Examples 2-8 to 2-14. As a result, Examples 2-8 to 2-14 were found to show no changes immediately after the production and after 8 hours passed in all the beverages so that there were no changes in the properties and states of the original beverages, whereas in the control product, ubidecarenone floated immediately after the production so that ubidecarenone crystals were precipitated out when 8 hours passed in all the beverages.

It was confirmed that the ubidecarenone preparation-containing food of the present invention has totally the same properties and states as the original food, and is enriched with ubidecarenone without changing the properties and states at all. Especially, the inherent transparency was not lost in the transparent beverages of the present invention. This is due to the effect of the ubidecarenone preparation of the present invention contained in the ubidecarenone preparation-containing food of the present invention. Specifically, it is considered that this is due to the fact that the ubidecarenone preparation of the present invention forms a complex matrix of three compounds, polyhydric alcohol-fatty acid esters which have contradictory properties in polarity of being hydrophilic and lipophilic, and the ubidecarenone, and forms a nanocapsule (average emulsion particle size: 10 to 150 nm) stabilized by the hydrophilic polyhydric alcohol-fatty acid ester. Here, it could be confirmed that since the ubidecarenone preparation of the present invention can be added to an aqueous system, there is no difficulty accompanied in the production of the ubidecarenone preparation-containing food of the present invention, showing versatility for foods.

Test Example 2-3

<Effect of the Ubidecarenone Preparation-Containing Foods>

Thirty-four healthy men and 16 healthy women of 22 to 51 years old (average age: 36.7, average weight: 58.6 kg) as test subjects were asked to take 100 ml of the ubidecarenone preparation-containing food of Example 2-5 (ubidecarenone content: 5 mg) three times a day, in the morning, at noon and in the evening (ubidecarenone: 15 mg/day) for 2 weeks. The evaluation was carried out according to the following evaluation criteria. Separately, the same 50 individuals were subjected to the same test using a food prepared by excluding the ubidecarenone preparation of Example 2-1 from the ubidecarenone preparation-containing food of Example 2-5 (control food).

<Evaluation Criteria>

Physically feeling much better as compared to that before taking: 2 points

Physically feeling better as compared to that before taking: 1 point

Unchanged as compared to that before taking: 0 points

Physically feeling worse as compared to that before taking: −1 point

Physically feeling much worse as compared to that before taking: −2 points

As a result, the average score was 1.64 points, no one scoring a minus evaluation when the ubidecarenone preparation-containing food of the present invention was taken, whereas the average score of all the test subjects was 0.06 when the control food was taken. This is due to the effect of the ubidecarenone preparation of the present invention contained in the ubidecarenone preparation-containing food of the present invention. Specifically, although it is deduced that ubidecarenone forms a complex with a lipophilic polyhydric alcohol-fatty acid ester and the complex is further enveloped in a nano-emulsion particles comprising a hydrophilic polyhydric alcohol-fatty acid ester, it is suggested that ubidecarenone is released from the complex in a body. Therefore, the ubidecarenone preparation of the present invention is a preparation which does not lose the effect inherently owned by ubidecarenone on a human body while constructing a system which can be stably added to an aqueous system, which is a feature of the food of the present invention. Here, since it is deduced that the ubidecarenone in the food of the present invention is included in fine emulsion particles having sizes of from 10 to 150 nm, it is considered that the bioabsorbability of the ubidecarenone is also enhanced.

Industrial Applicability

According to the present invention, a CoQ10-containing composition suitably utilizable for applications in foods, which has excellent stability and improved bioabsorbability of CoQ10. The composition can be easily handled upon food processing, added to an aqueous system, and applied especially to a transparent beverage. Therefore, the present invention makes a significant contribution to the future health-food industries, rendering very large industrial significance.

The invention claimed is:

1. A coenzyme Q10-containing composition comprising:
   a coenzyme Q10, and
   a hydrophilic fatty acid ester of a polyhydric alcohol, wherein said hydrophilic fatty acid ester of the polyhydric alcohol comprises an ester of monoglycerol with a fatty acid and an organic acid, wherein the organic acid is selected from the group consisting of citric acid, acetic acid, succinic acid, lactic acid and diacetyltartaric acid, and the fatty acid is selected from the group consisting of stearic acid, caprylic acid and oleic acid,
   wherein said ester of monoglycerol with the fatty acid and the organic acid has an HLB of 8 or more,
   wherein the total content of the coenzyme Q10 and the hydrophilic fatty acid ester of the polyhydric alcohol is from 1 to 60% by weight,
   wherein the amount of the hydrophilic fatty acid ester of the polyhydric alcohol is from 40 to 3,500 parts by weight, based on 100 parts by weight of the coenzyme Q10, and
   wherein the composition is emulsified or solubilized in an oil-in-water droplet form.

2. The coenzyme Q10-containing composition of claim 1, wherein the composition has higher bioabsorbability of coenzyme Q10 as compared to that of coenzyme Q10 alone.

3. The coenzyme Q10-containing composition of claim 1, further comprising an ester of polyglycerol with condensed ricinoleic acid.

4. The coenzyme Q10-containing composition of claim 1, wherein the composition is dried to be in the form of a granule or powder, to give a granular or powder product of the oil-in-water emulsion type coenzyme Q10-containing composition.

5. A coenzyme Q10-containing composition comprising:
   a coenzyme Q10,
   a lipophilic fatty acid ester of a polyhydric alcohol, and
   a hydrophilic fatty acid ester of the polyhydric alcohol, wherein said hydrophilic fatty acid ester of the polyhydric alcohol comprises an ester of monoglycerol with a fatty acid and an organic acid, wherein the organic acid is selected from the group consisting of citric acid, acetic acid, succinic acid, lactic acid and diacetyltartaric acid, and the fatty acid is selected from the group consisting of stearic acid, caprylic acid and oleic acid,
   wherein said ester of monoglycerol with the fatty acid and the organic acid has an HLB of 8 or more,
   wherein the total content of the coenzyme Q10, the lipophilic fatty acid ester of the polyhydric alcohol and the hydrophilic fatty acid ester of the polyhydric alcohol is from 2 to 60% by weight,
   wherein the amount of the lipophilic fatty acid ester of the polyhydric alcohol is from 25 to 2,000 parts by weight, based on 100 parts by weight of the coenzyme Q10,
   wherein the amount of the hydrophilic fatty acid ester of the polyhydric alcohol is from 50 to 10,000 parts by weight, based on 100 parts by weight of the coenzyme Q10, and
   wherein the composition is emulsified or solubilized in an oil-in-water droplet form.

6. The coenzyme Q10-containing composition of claim 5 produced by the following steps: a first step of forming a complex between the coenzyme Q10 and the lipophilic fatty acid ester of the polyhydric alcohol; and a second step of mixing the complex obtained in the first step with the hydrophilic fatty acid ester of the polyhydric alcohol, wherein the resulting composition is emulsified or solubilized in an oil-in-water droplet form.

7. The coenzyme Q10-containing composition of claim 5, wherein the lipophilic fatty acid ester of the polyhydric alcohol has an HLB of 6 or less, and the hydrophilic fatty acid ester of the polyhydric alcohol has an HLB of 8 or more.

8. The coenzyme Q10-containing composition of claim 5, further comprising an ester of polyglycerol with condensed ricinoleic acid.

9. The coenzyme Q10-containing composition of claim 5, wherein the composition is dried to be in the form of a granule or powder, to give a granular or powder product of the oil-in-water emulsion type coenzyme Q10-containing composition.

10. The coenzyme Q10-containing composition of claim 5 or 6, wherein the emulsion particles have an average emulsion particle size of 330 nm or less.

11. The coenzyme Q10-containing composition of claim 6, further comprising a step of drying the composition in order to form a granule or powder, to give a granular or powder product of the oil-in-water emulsion type coenzyme Q10-containing composition.

* * * * *